US010308936B2

(12) United States Patent
Nakaki et al.

(10) Patent No.: US 10,308,936 B2
(45) Date of Patent: Jun. 4, 2019

(54) MIR-96-5P INHIBITOR AND A SCREENING METHOD FOR THE INHIBITOR

(71) Applicant: TEIKYO UNIVERSITY, Tokyo (JP)

(72) Inventors: Toshio Nakaki, Tokyo (JP); Chisato Kinoshita, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 0 days.

(21) Appl. No.: 15/486,648

(22) Filed: Apr. 13, 2017

(65) Prior Publication Data

US 2017/0218364 A1   Aug. 3, 2017

Related U.S. Application Data

(62) Division of application No. 14/870,655, filed on Sep. 30, 2015, now abandoned.

(30) Foreign Application Priority Data

Oct. 8, 2014 (JP) ................................ 2014-207297

(51) Int. Cl.
*C12N 15/113* (2010.01)
*G01N 33/50* (2006.01)
*C12N 15/11* (2006.01)

(52) U.S. Cl.
CPC .......... *C12N 15/113* (2013.01); *C12N 15/111* (2013.01); *G01N 33/5023* (2013.01); *G01N 33/5058* (2013.01); *C12N 2310/113* (2013.01); *C12N 2310/141* (2013.01); *C12N 2320/10* (2013.01)

(58) Field of Classification Search
CPC .. C12N 15/111; C12N 15/113; A01K 2207/05
See application file for complete search history.

(56) References Cited

U.S. PATENT DOCUMENTS 7,683,036 B2    3/2010  Esau
2009/0162886 A1  6/2009  Nakaki et al.

OTHER PUBLICATIONS

Johnson et al. Nutrients 4:1399-1440 (Year: 2012).*
Tan J-KY, Sellers DL, Pham B, Pun SH and Homer PJ (2016) Non-Viral Nucleic Acid Delivery Strategies to the Central Nervous System. Front. Mol. Neurosci. 9:108. pp. 1-13 (Year: 2016).*
Laura A. Sena et al., "Physiological Roles of Mitochondrial Reactive Oxygen Species", Molecular Cell Review, Oct. 26, 2012, vol. 48, pp. 158-167.
Masahiko Watabe et al., "Regulation of Glutathione Synthesis via Interaction between Glutamate Transport-Associated Protein 3-18 (GTRAP3-18) and Excitatory Amino Acid Carrier-1 (EAAC1) at Plasma Membrane", Molecular Pharmacology, 2007, vol. 72, No. 5, pp. 1103-1110.
Maged M. Harraz et al., "MicroRNAs in Parkinson's disease", Journal of Chemical Neuroanatomy, 2011, vol. 42, pp. 127-130.
Hai-Ying Mary Cheng et al., "Revealing a Role of MicroRNAs in the Regulation of the Biological Clock", Cell Cycle, Dec. 15, 2007, vol. 6, No. 24, pp. 3034-3038.
L. David Willison et al., "Circadian dysfunction may be a key component of the non-motor symptoms of Parkinson's disease: Insights from a trasgenic mouse model", Experimental Neurology, 2013, vol. 243, pp. 57-66.
Roman V. Kondratov et al., "Early aging and age-related pathologies in mice deficient in BMAL1, the core component of the circadian clock", Genes & Development, 2006, vol. 20, pp. 1868-1873.
Ari E. Berman et al., "N-Acetylcysteine Prevents Loss of Dopaminergic Neurons in the EAAC1 -/- Mouse", Annals of Neurology, 2011, vol. 69, No. 3, pp. 509-520.
Nicholas J. Maragakis et al., "Glutamate transporterstransportersanimal models to neurologic disease", Neurobiology of Disease, 2004, Vo. 15, pp. 461-473.
Jeswinder Sian et al., "Alterations in Glutathione Levels in Parkinson's Disease and Other Neurodegenerative Disorders Affecting Basal Ganglia", Annals of Neurology, 1994, vol. 36, No. 3, pp. 348-355.
Chisato Kinoshita et al., "Rhythmic oscillations of the microRNA miR-96-5p play a neuroprotective role by indirectly regulating glutathione levels", Nature Communications, May 7, 2014, 5:3823 doi 10.1038/ncomms4823, pp. 1-10.
Ralf Dringen, "Metabolism and functions of glutathione in brain", Progress in Neurobiology, 2000, vol. 62, pp. 649-671.

* cited by examiner

*Primary Examiner* — Brian Whiteman
(74) *Attorney, Agent, or Firm* — Wenderoth, Lind & Ponack, L.L.P.

(57) ABSTRACT

The present invention provides novel medical means to facilitate glutathione (GSH) synthesis in the brain. These means are miR-96-5p inhibitor increasing GSH expression in the brain and a pharmaceutical composition comprising the miR-96-5p inhibitor and having a preventive and/or therapeutic performance to a disease caused by decrease of GSH amount or depression of GSH activity.

5 Claims, 6 Drawing Sheets
(1 of 6 Drawing Sheet(s) Filed in Color)
Specification includes a Sequence Listing.

SEQUENCE LISTING

<160> NUMBER OF SEQ ID NOS: 12

<210> SEQ ID NO 1
<211> LENGTH: 23
<212> TYPE: RNA
<213> ORGANISM: Homo sapiens

<400> SEQUENCE: 1
uuuggcacua gcacauuuuu gcu                                          23

<210> SEQ ID NO 2
<211> LENGTH: 21
<212> TYPE: RNA
<213> ORGANISM: Homo sapiens

<400> SEQUENCE: 2
uacaguacug ugauaacuga a                                            21

<210> SEQ ID NO 3
<211> LENGTH: 23
<212> TYPE: RNA
<213> ORGANISM: Homo sapiens

<400> SEQUENCE: 3
cccaguguuc agacuaccug uuc                                          23

<210> SEQ ID NO 4
<211> LENGTH: 22
<212> TYPE: RNA
<213> ORGANISM: Homo sapiens

<400> SEQUENCE: 4
uaacacuguc ugguaacgau gu                                           22

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 5
gggagctcat aggccggccc ctggctgcag atg                               33

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 6
gcacgcgtct atgccgaaag aatgagggaa gtgtt                             35

<210> SEQ ID NO 7
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 7
gggagctcat aggccatgcc tgacctcaga ttga                              34

```
<210> SEQ ID NO 8
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 8
gcacgcgtct atgcctaagg ggagaaagag tggg                              34

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
taatgtcgga aaatgtcaat ttttaac                                      27

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 10 ggacagggt caattacagc cttttac                                       27

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
caatgttgag tattgggacg ctggtaa                                      27

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 12
cctaagaaaa aagttacaac tcataac                                      27
```

MIR-96-5P INHIBITOR AND A SCREENING METHOD FOR THE INHIBITOR

FIELD

The instant invention relates to a miR-96-5p inhibitor, which has a positive function for a biosynthesis of an antioxidant, glutathione (GSH), a pharmaceutical composition comprising the inhibitor, and a method for screening a novel substance inhibiting the miR-96-5p.

BACKGROUND

The balance between oxidants and antioxidants is a key factor for normal brain function (Non Patent Literature 1). The imbalance of redox states caused by an excess of oxidants and/or a depletion of antioxidants is defined as an oxidative-stress state (Non Patent Literature 2). Glutathione is an especially important antioxidant in the central nervous system because of the lower activity of major antioxidant enzymes such as superoxide dismutase and catalase in the brain (Non Patent Literature 3). Glutathione exists in both a reduced form (GSH) and an oxidized form (GSSG), functioning in various redox reactions. Depletion of GSH in the brain is a known cause of neurodegenerative diseases (NDs) such as Parkinson's disease (PD). PD is characterized by a selective loss of dopaminergic neurons in the substantia nigra pars compacta (SNc) (Non Patent Literature 4). A decrease of GHS is also observed in various diseases such as malignant tumors and infectious diseases and so on.

GSH is a tripeptide composed of cysteine, glutamate and glycine (Non Patent Literature 5). Among these amino acids, cysteine is the rate-limiting factor, since the concentrations of glutamate and glycine in neurons are sufficient. Although cystine is generally known as a source of cysteine, neurons do not express the cystine transport system in mature brains, and thus cysteine is considered a major determinant for intracellular GSH synthesis in neurons.

One of the important factors regulating GSH synthesis is excitatory amino acid carrier 1 (EAAC1), a member of the sodium-dependent excitatory amino acid transporter (EAAT) family. Unlike other EAATs, EAAC1 is selectively enriched in the neurons of the central nervous system (Non Patent Literature 6). It was indicated that the transport of cysteine, rather than that of glutamate, is the major function of EAAC1 (Non Patent Literatures 7 and 8). In fact, EAAC1 deficiency decreased the neuronal GSH content and increased markers of neuronal oxidative stress in the mouse brain (Non Patent Literature 9).

The circadian clock is an internal timekeeping system that allows organisms to adapt physiological and behavioral processes to environmental light/dark cycles (Non Patent Literature 10). Almost all organisms harbor this system, indicating that the circadian clock developed early in the evolution of life. In mammals, the master clock is located in the suprachiasmatic nucleus (SCN). The SCN drive endogenous rhythms and control circadian rhythms in peripheral tissues, including other brain areas such as the SNc (Non Patent Literature 11). The circadian system is regulated by several clock genes such as transcriptional activators (e.g., CLOCK and BMAL1) and repressors (e.g., PER1 and 2). It was shown that BMAL1-deficient mice exhibit increased levels of reactive oxygen species (ROS) and accelerated aging, suggesting that the circadian clock is involved in ROS regulation (Non Patent Literature 12). It was also reported that sleep disorders and circadian disruptions are common in PD patients, and that their symptoms display diurnal fluctuations (Non Patent Literature 13). Together, these reports prompt the interesting theory that there may be a significant correlation between disruption of the circadian system and the misregulation of ROS homeostasis. The mechanism of this association has long been elusive, however.

MicroRNA (miRNA) is a class of small, non-coding molecules that are involved in the post-transcriptional regulation of target gene expression (Non Patent Literature 14). Many miRNAs are highly conserved across species. The sequence in the seed region, which is defined as two to eight nucleotides of miRNA, is the key for determining the target. It has been suggested that miRNAs play important roles in regulating protein levels that exhibit circadian rhythmicity (Non Patent Literature 15). A proteomic analysis in mouse liver revealed that up to 20% of the soluble proteins are rhythmic whereas only 10% of the mRNA is rhythmic (Non Patent Literature 16), suggesting the possible involvement of post-transcriptional regulation such as miRNA regulation. Moreover, several reports have shown that PD-related genes are also regulated by miRNAs (Non Patent Literature 17). Taken together, these findings suggest complicated connections among circadian systems, PD-related gene expression and miRNA regulation, but such connections have not yet been studied.

The present inventors have already proposed a method for screening a substance decreasing an expression of GTRAP3-18 which has a negative function for glutathione synthesis, i.e, a substance promoting glutathione synthesis (Patent Literature 1). As a micro RNA inhibitor and a pharmaceutical composition comprising the inhibitor, for example, a micro RNA inhibitor targeting a gene of tumor-suppression factor and an anti-tumor pharmaceutical composition are known (Patent Literature 2). Regarding to a method for screening a micro RNA inhibitor (antagonist), for example, a screening method of miRNA-29 antagonist is known (Patent Literature 3). In addition, as a nucleic acid medicine such as oligonucleotide, Patent Literature 4 discloses a technique for directing a small interfering RNA (siRNA) to neurons.

CITATION LIST

Patent Literature

1. WO2007/129598 (U.S. Pat. No. 8,551,711)
2. JP 2014-515024A
3. JP 2013-523696A
4. JP 2013-529181A

Non Patent Literature

1. Henchcliffe, C. & Beal, M. F. Mitochondrial biology and oxidative stress in Parkinson disease pathogenesis. Nat Clin Pract Neurol 4, 600-9 (2008).
2. Finkel, T. & Holbrook, N. J. Oxidants, oxidative stress and the biology of ageing. Nature 408, 239-47 (2000).
3. Dringen, R. Metabolism and functions of glutathione in brain. Prog Neurobiol 62, 649-71 (2000).
4. Sian, J. et al. Alterations in glutathione levels in Parkinson's disease and other neurodegenerative disorders affecting basal ganglia. Ann Neurol 36, 348-55 (1994).
5. Aoyama, K., Watabe, M. & Nakaki, T. Regulation of neuronal glutathione synthesis. J Pharmacol Sci 108, 227-38 (2008).
6. Maragakis, N. J. & Rothstein, J. D. Glutamate transporters: animal models to neurologic disease. Neurobiol Dis 15, 461-73 (2004).

7. Rothstein, J. D. et al. Knockout of glutamate transporters reveals a major role for astroglial transport in excitotoxicity and clearance of glutamate. Neuron 16, 675-86 (1996).
8. Aoyama, K. et al. Neuronal glutathione deficiency and age-dependent neurodegeneration in the EAAC1 deficient mouse. Nat Neurosci 9, 119-26 (2006).
9. Berman, A. E. et al. N-acetylcysteine prevents loss of dopaminergic neurons in the EAAC1-/- mouse. Ann Neurol 69, 509-20 (2011).
10. Bass, J. Circadian topology of metabolism. Nature 491, 348-56 (2012).
11. Kondratov, R. V. A role of the circadian system and circadian proteins in aging. Ageing Res Rev 6, 12-27 (2007).
12. Kondratov, R. V., Kondratova, A. A., Gorbacheva, V. Y., Vykhovanets, O. V. & Antoch, M. P. Early aging and age-related pathologies in mice deficient in BMAL1, the core component of the circadian clock. Genes Dev 20, 1868-73 (2006).
13. Willison, L. D., Kudo, T., Loh, D. H., Kuljis, D. & Colwell, C. S. Circadian dysfunction may be a key component of the non-motor symptoms of Parkinson's disease: insights from a transgenic mouse model. Exp Neurol 243, 57-66 (2013).
14. Bartel, D. P. MicroRNAs: target recognition and regulatory functions. Cell 136, 215-33 (2009).
15. Cheng, H. Y. & Obrietan, K. Revealing a role of microRNAs in the regulation of the biological clock. Cell Cycle 6, 3034-5 (2007).
16. Reddy, A. B. et al. Circadian orchestration of the hepatic proteome. Curr Biol 16, 1107-15 (2006).
17. Harraz, M. M., Dawson, T. M. & Dawson, V. L. MicroRNAs in Parkinson's disease. J Chem Neuroanat 42, 127-30 (2011).
18. Calcutt, G. Diurnal variations in rat blood glutathione levels. Naturwissenschaften 54, 120 (1967).
19. Filipski, E. et al. Persistent twenty-four hour changes in liver and bone marrow despite suprachiasmatic nuclei ablation in mice. Am J Physiol Regul Integr Comp Physiol 287, R844-51 (2004).
20. Blanco, R. A. et al. Diurnal variation in glutathione and cysteine redox states in human plasma. Am J Clin Nutr 86, 1016-23 (2007).
21. Lach, H., Surowiak, J., Dziubek, K., Krawczyk, S. & Szaroma, W. Cosinor analysis of diurnal changes of the reduced glutathione level in the blood, brain, liver and kidneys of mice, induced by ACTH administration. Acta Biol Hung 37, 93-100 (1986).
22. Farooqui, M. Y. &Ahmed, A. E. Circadian periodicity of tissue glutathione and its relationship with lipid peroxidation in rats. Life Sci 34, 2413-8 (1984).
23. Baydas, G. et al. Daily rhythm of glutathione peroxidase activity, lipid peroxidation and glutathione levels in tissues of pinealectomized rats. Neurosci Lett 323, 195-8 (2002).
24. Balsalobre, A., Damiola, F. & Schibler, U. A serum shock induces circadian gene expression in mammalian tissue culture cells. Cell 93, 929-37 (1998).
25. Akashi, M. & Nishida, E. Involvement of the MAP kinase cascade in resetting of the mammalian circadian clock. Genes Dev 14, 645-9 (2000).
26. Watabe, M., Aoyama, K. & Nakaki, T. Regulation of glutathione synthesis via interaction between glutamate transport-associated protein 3-18 (GTRAP3-18) and excitatory amino acid carrier-1 (EAAC1) at plasma membrane. Mol Pharmacol 72, 1103-10 (2007).
27. Aoyama, K. et al. Increased neuronal glutathione and neuroprotection in GTRAP3-18-deficient mice. Neurobiol Dis 45, 973-82 (2012).
28. Sena, L. A. & Chandel, N. S. Physiological roles of mitochondrial reactive oxygen species. Mol Cell 48, 158-67 (2012).
29. Dickinson, B. C. & Chang, C. J. Chemistry and biology of reactive oxygen species in signaling or stress responses. Nat Chem Biol 7, 504-11 (2011).
30. Arjona, A. & Sarkar, D. K. Circadian oscillations of clock genes, cytolytic factors, and cytokines in rat NK cells. J Immunol 174, 7618-24 (2005).
31. Kochman, L. J., Weber, E. T., Fornal, C. A. & Jacobs, B. L. Circadian variation in mouse hippocampal cell proliferation. Neurosci Lett 406, 256-9 (2006).
32. Ma, D., Panda, S. & Lin, J. D. Temporal orchestration of circadian autophagy rhythm by C/EBPbeta. Embo J 30, 4642-51 (2011).
33. Kondratova, A. A., Dubrovsky, Y. V., Antoch, M. P. & Kondratov, R. V. Circadian clock proteins control adaptation to novel environment and memory formation. Aging (Albany N.Y.) 2, 285-97 (2010).
34. Beaver, L. M. et al. Circadian regulation of glutathione levels and biosynthesis in *Drosophila melanogaster*. PLoS One 7, e50454 (2012).
35. Xu, Y. Q. et al. Diurnal variation of hepatic antioxidant gene expression in mice. PLoS One 7, e44237 (2012).
36. Krishnan, N., Davis, A. J. & Giebultowicz, J. M. Circadian regulation of response to oxidative stress in *Drosophila melanogaster*. Biochem Biophys Res Commun 374, 299-303 (2008).
37. Pablos, M. I. et al. Rhythms of glutathione peroxidase and glutathione reductase in brain of chick and their inhibition by light. Neurochem Int 32, 69-75 (1998).
38. Jomova, K., Vondrakova, D., Lawson, M. & Valko, M. Metals, oxidative stress and neurodegenerative disorders. Mol Cell Biochem 345, 91-104 (2010).
39. Sofic, E. L., K. W., Jellinger, K., Riederer, P. Reduced and oxidized glutathione in the substantia nigra of patients with Parkinson's disease. Neurosci Lett 142, 128-130 (1992).
40. Perry, T. L. G., D. V., Hansen, S. Parkinson's disease: A disorder due to nigral glutathione deficiency? Neurosci Lett 33, 305-310 (1982).
41. Tomita, J., Nakajima, M., Kondo, T. & Iwasaki, H. No transcription-translation feedback in circadian rhythm of KaiC phosphorylation. Science 307, 251-4 (2005).
42. Nakajima, M. et al. Reconstitution of circadian oscillation of cyanobacterial KaiC phosphorylation in vitro. Science 308, 414-5 (2005).
43. O'Neill, J. S. & Reddy, A. B. Circadian clocks in human red blood cells. Nature 469, 498-503 (2011).
44. Kondratov, R. V., Vykhovanets, O., Kondratova, A. A. &Antoch, M. P. Antioxidant N-acetyl-L-cysteine ameliorates symptoms of premature aging associated with the deficiency of the circadian protein BMAL1. Aging (Albany N.Y.) 1, 979-87 (2009).
45. Aoyama, K., Matsumura, N., Watabe, M. & Nakaki, T. Oxidative stress on EAAC1 is involved in MPTP-induced glutathione depletion and motor dysfunction. Eur J Neurosci 27, 20-30 (2008).
46. Matsumura, N. et al. Anticonvulsant action of indazole. Epilepsy Res 104, 203-16 (2013).

SUMMARY

Technical Problem

As described above, the glutathione, a brain antioxidant, relates to various diseases, and especially, depletion of brain glutathione is a cause of neurodegenerative diseases due to decrease of neuroprotection against oxidative stress.

The technical problem of the instant invention, therefore, is to provide a new medical means for promoting glutathione synthesis in the brain.

Solution to Problem

The inventors have intently studied the above problem, and obtained the following novel findings as hereinafter disclosed in Examples:

GSH levels display a diurnal rhythm which is correlated with neuroprotective activity against oxidative stress in dopaminergic cells;

A rhythmic expression of EAAC1, an important regulator of GSH synthesis, is negatively regulated by an miRNA, miR-96-5p, which also exhibits a diurnal rhythm; and The intracerebroventricular (i.c.v.) injection of a miR-96-5p inhibitor significantly increased the GSH level, EAAC1 expression and neuroprotection against oxidative stress in the mouse brain in vivo.

Based on the above findings, the present application provides the following inventions.

(1) A miR-96-5p inhibitor increasing an expression of glutathione (GSH) in the brain.
(2) The miR-96-5p inhibitor in (1), which is an oligonucleotide at least partially complementary to the nucleotide sequence of SEQ ID NO: 1.
(3) The miR-96-5p inhibitor in (2), which is an antisense oligonucleotide for the sequence of SEQ ID. NO: 1.
(4) A pharmaceutical composition comprising the miR-96-5p inhibitor of any one of (1) to (3), which has a preventive and/or therapeutic performance to a disease caused by decrease of GSH amount or depression of GSH activity.
(5) The pharmaceutical composition in (4), wherein the disease is a neurodegenerative disease caused by an oxidative stress in the brain.
(6) A screening method for a substance inhibiting an activity of miR-96-5p, which comprises:
  (a) identifying a candidate substance capable of binding with miRNA-96-5p;
  (b) contacting the candidate substance with a cell expressing excitatory amino acid carrier 1 (EAAC1) and miRNA-96-5p; and
  (c) measuring expression level at least one of glutathione and EAAC1, and deciding the candidate substance of which measurement in (c) is increased compared with a control measurement as a target substance.
(7) The screening method in (6), wherein the cell is one within the brain of non-human animal.

In the present invention, the "increase of expression" of glutathione (GSH) means an increase of GSH amount in a cell, an increase of transcription level of a gene encoding a protein which controls intracellular concentration of GSH, or an increase of GSH amount induced from the gene transcript. The "Activity" of GSH means an antioxidant activity, or neuroprotective effects against an oxidative-stress (ex. inhibition of apoptosis). The inhibition of miR-96-5p means to inhibit a binding of miR-96-5p with EAAC1 3'-UTR, or inhibit a suppression of EAAC1 expression by EAAC1.

Advantageous Effects of Invention

According to the present invention, a novel therapeutic agent for various diseases caused by decrease of GSH amount or its activity, especially for neurodegenerative diseases caused by decease of neuroprotective effects against an oxidative-stress.

BRIEF DESCRIPTION OF DRAWINGS

The patent or application file contains at least one drawing executed in color. Copies of this patent or patent application publication with color drawing(s) will be provided by the office upon request and payment of the necessary fee.

DESCRIPTION OF EMBODIMENTS

Figure 1:
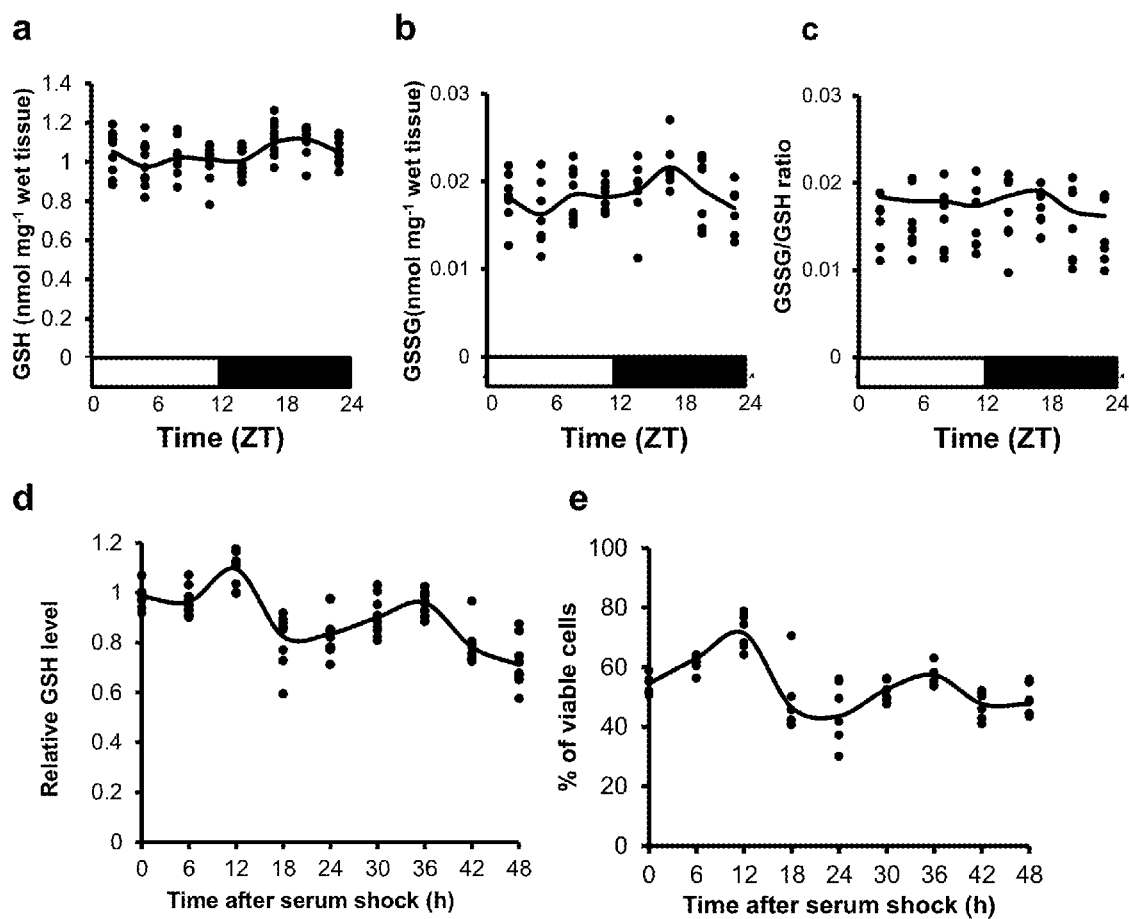
FIG. 1. The diurnal variation of GSH level is correlated with that of protective activity against oxidative stress. (a) Diurnal changes in GSH levels in the mesencephalon (n=10, each point). The bars below the graphs indicate the light (white) and dark (black) periods. The data in the figure represent mean values and individual data points. Data were analyzed by one-way ANOVA and cosinor analysis. A significant rhythmicity was detected (P=0.00018). (b) Diurnal changes in the GSSG levels in the mesencephalon (n=8, each point). Data were analyzed by one-way ANOVA and cosinor analysis. Significant rhythmicity (P=0.0021) was observed. (c) Individual data points representing the ratio of GSSG to GSH levels in each sample (n=8, each point). Data were analyzed by one-way ANOVA and cosinor analysis. No significant diurnal rhythm was observed (P=0.57). (d) Rhythmic changes of GSH levels in serum-shocked SH-SY5Y cells (n=10, each point). Data represent mean values and individual data points. Data were analyzed by one-way ANOVA and cosinor analysis. A significant circadian variation (P=0.00023) was observed. (e) Time-dependent changes of viable cell percentages after $H_2O_2$ treatment for 2 h at each time point (n=7). Data were analyzed by one-way ANOVA and cosinor analysis. Significant rhythmicity was revealed (P=0.0003). The number of individual data points is the same as the sample size although some points overlap.

MiR-96-5p, the object for inhibition in the present invention, is a micro RNA controlling EAAC1 expression by targeting EAAC1-3'-UTR, and has the nucleotide sequence in SEQ ID NO:1 (5'-uuuggcacuagcacauuuuugcu-3'). One embodiment of the miR-96-5p inhibitor of the present invention is an oligonucleotide at least partially complementary to the nucleotide sequence of SEQ ID NO: 1, and preferably an antisense oligonucleotide complementary to the nucleotide sequence of SEQ ID. NO:1. The definition "at least partially complementary" means at least 75%, preferably 85%, more preferably 95% complementary to the nucleotide sequence of SEQ ID NO:1 on the condition annealing with the miR-96-5p. The "antisense oligonucleotide" is 100% complementary to the nucleotide sequence of SEQ ID NO:1.

The miR-96-5p inhibitor (oligonucleotide) may be produced, for example, using known chemical synthesis methods, or enzymatic transcription methods. Examples of the known chemical synthesis methods include the phosphoramidite method, the phosphorothioate method, and the phosphotriester method. For example, the AB13900 high throughput nucleic acid synthesizer (Applied Biosystems), the NTS H-6 nucleic acid synthesizer (Nihon Techno Service Co., Ltd.), and the OligoPilot 10 nucleic acid synthesizer (GE Healthcare) may be used for the synthesis. As an example of the enzymatic transcription methods, a transcription method may be used that uses an RNA polymerase, such as T7, T3, and SP6RNA polymerases, using a template plasmid or DNA having a base sequence of interest. The oligonucleotide produced by the chemical synthesis or transcription is purified by HPLC or the like.

Any nucleic acid may be used for the miR-96-5p (oligonucleotide) of the present invention, provided that it is a molecule formed by polymerization of a nucleotide or a functionally equivalent molecule thereof. Examples of the nucleotide include a ribonucleotide polymer RNA, a deoxyribonucleotide polymer DNA, a mixed polymer of RNA and DNA, and a nucleotide polymer containing a nucleotide analog.

Examples of the nucleotide analog include molecules produced by modifying ribonucleotides, deoxyribonucleotides, or RNAs or DNAs to provide improved affinity to the target miR-96-5p, improved cell permeability, or better visualization compared to RNAs or DNAs. Specific examples include sugar-modified nucleotide analogs, and phosphodiester bond-modified nucleotide analogs.

The sugar-modified nucleotide analogs may be any molecules, as long as the chemical structure of the nucleotide sugar has the chemical structure of a substance added or substituted with respect to the sugar either in part or as a whole. Examples include nucleotide analogs substituted with 2'-O-methylribose, nucleotide analogs substituted with 2'-O-propylribose, nucleotide analogs substituted with 2'-methoxyethoxyribose, nucleotide analogs substituted with 2'-O-methoxyethylribose, nucleotide analogs substituted with 2'-O-[2-(guanidium)ethyl]ribose, nucleotide analogs substituted with 2'-O-fluororibose, bridged synthetic nucleic acids (Bridged Nucleic Acids; BNAs) having two cyclic structures after introduction of a bridged structure to the sugar moiety, more specifically locked synthetic nucleic acids (Locked Nucleic Acids; LNAs) having a bridge connecting the 2'-position oxygen atom and the 4'-position carbon atom via methylene, and ethylene bridged synthetic nucleic acid (ethylene bridged nucleic acids; ENAs) [Nucleic Acid Research, 32, e175 (2004)]. Other examples include peptide nucleic acids (PNAs) [Acc. Chem. Res., 32, 624 (1999)], oxypeptide nucleic acids (OPNAs) [J. Am. Chem. Soc., 123, 4653 (2001)], and peptide ribonucleic acids (PRNAs) [J. Am. Chem. Soc., 122, 6900 (2000)].

The phosphodiester bond-modified nucleotide analogs may be any molecules, as long as the chemical structure of the nucleotide phosphodiester bond has a substance added or substituted with respect to the phosphodiester bond either in part or as a whole. Examples include nucleotide analogs having a substituted phosphorothioate bond, and nucleotide analogs having a substituted N3'-P5' phosphoramidate bond.

Further, the nucleotide analog may be one in which the atoms (for example, hydrogen atom, oxygen atom), or the functional groups (for example, hydroxyl group, amino group) in the base moiety, the ribose moiety, and the phosphodiester bond moiety of the nucleic acid are substituted by other atoms (for example, hydrogen atom, sulfur atom), functional groups (for example, amino group), or alkyl groups of 1 to 6 carbon atoms, or protected by protecting groups (for example, methyl group, or acyl group). Molecules obtained by addition of other chemical substances, for example, such as lipids, phospholipids, phenazine, folate, phenanthridine, anthraquinone, acridine, fluorescein, rhodamine, coumalin, and dyes to nucleic acid also may be used.

Examples of the molecules obtained by addition of other chemical substances to nucleic acid include 5'-polyamine adduct derivatives, cholesterol adduct derivatives, steroid adduct derivatives, bile acid adduct derivatives, vitamin adduct derivatives, Cy5 adduct derivatives, Cy3 adduct derivatives, 6-FAM adduct derivatives, and biotin adduct derivatives. Alternatively, as a nucleotide analog or a nucleotide derivative for the miR-96-5p (oligonucleotide) of the invention, those disclosed in Patent Literatures 2 and 4 may be also used.

The pharmaceutical composition of the present invention may be prepared in a form delivering the miR-96-5p inhibitor (oligonucleotide) into the brain. Technology to deliver a nucleic acid pharmaceutical in the brain is known, for example, in Patent Literature 4 and the like. For example, one embodiment is a recombinant expression vector of which an insert is DNA encoding miR-96-5p inhibitor (oligonucleotide). More precisely, constructing a recombinant expression vector by linking the oligonucleotide with a transcriptional regulatory sequence (promoter) having an activity in the brain cells (neurons and glial cells), and expressing the miR-96-5p inhibitor (oligonucleotide) in the brains by administering the vector in vivo.

Another embodiment of the pharmaceutical composition is an administration of DNA itself (naked DNA). The administration protocol of naked DNA is, for example, described in WO90/11092 and U.S. Pat. No. 5,580,859. Uptake efficiency of naked DNA can be improved by using a biodegradable latex bead. DNA coating latex bead can be efficiently transferred into a cell after the onset of endocytosis. This method would be further improved by treating the bead to increase its hydrophobicity, thereby promoting endosome disruption and discharge of DNA into cytoplasm.

As a carrier for transferring the miR-96-5p inhibitor (oligonucleotide) into a cell, a liposome or lipid (for example, U.S. Pat. Nos. 7,001,614, 7,067,697, and 7,214,384), and a synthetic polymer (for example, U.S. Pat. No. 6,312,727) may be used.

The therapeutic composition of the present invention may be prepared in a form of solid, semisolid, liquid or gas which includes as a tablet, a capsule, a powder, a granule, an ointment, a solution, a suppository, an injection, an inhalation and an aerosol, with a combination with a pharmacologically acceptable carrier or diluents.

It is desirable to use an administration route most effective for the treatment, and the route may be, for example, an oral administration route, or a parenteral administration route such as buccal administration, airway administration, rectal administration, subcutaneous administration, intramuscular administration, and intravenous administration. Preferred is an oral administration.

Examples of preparations suitable for oral administration include an emulsion, a syrup, a capsule formulation, a tablet, a powder, and a granule. Liquid preparations such as an emulsion and a syrup may be produced with additives such as water, sugars (e.g., sucrose, sorbitol, and fructose), glycols (e.g., polyethylene glycol, and propylene glycol), oils (e.g., sesame oil, olive oil, and soybean oil), preservatives (e.g., p-hydroxybenzoic acid esters), and flavors (e.g., strawberry flavor, and peppermint flavor). Preparations such as a capsule formulation, a tablet, a powder, and a granule may be produced with additives such as excipients (e.g., lactose, glucose, sucrose, and mannitol), disintegrants (e.g., starch, and sodium alginate), lubricants (e.g., magnesium stearate, and talc), binders (e.g., polyvinyl alcohol, hydroxypropyl cellulose, and gelatin), surfactants such as fatty acid ester), and plasticizers (e.g., glycerine).

Examples of preparations suitable for parenteral administration include injections, suppositories, and aerosolized agents. The injections may be prepared using carriers such as a salt solution, a glucose solution, and a mixture of these. The suppositories may be prepared using carriers such as a cacao butter, a hydrogenated fat, and a carboxylic acid. The aerosolized agents may be prepared using carriers that do not stimulate the mouth and airway mucosa of a recipient, and that disperse the active ingredient in the form of fine particles to facilitate absorption. Specific examples of the carriers include lactose and glycerine. The preparations may be, for example, in the form of an aerosol, a dry powder, or the like as may be decided according to the properties of the miR-96-5p inhibitor and of the carrier used. The same components exemplified for the oral administration additives also may be used for the parenterally administered form.

The dose and the dosing intervals vary according to such factors as the intended therapeutic effect, the administration method, the duration of therapy, and the age and body weight. Typically, the dose is 10 g/kg/day to 20 mg/kg/day for adults. The dose may also be arranged so that the concentration of the miR-96-5p inhibitor (oligonucleotide) in the blood samples collected within the first 24-48 hours after administration of the drug. Furthermore, since GSH amount in the brain shows a diurnal fluctuation as described in the following examples, the pharmaceutical composition of the present invention is preferred to take for a particular time period when the GSH amount in the brain decreases.

The screening method of the present invention comprises the steps:

(a) identifying a candidate substance capable of binding with miRNA-96-5p;

(b) contacting the candidate substance with a cell expressing excitatory amino acid carrier 1 (EAAC1) and miRNA-96-5p; and (c) measuring expression level at least one of glutathione and EAAC1, and deciding the candidate substance of which measurement in (c) is increased compared with a control measurement as a target substance.

The screening method can be performed by a basic procedure disclosed in Patent Literatures 1 and 3. Examples of the candidate substance in step (a) may include organic or inorganic compounds (especially, low molecular compounds), proteins and peptides. The candidate substance may be also those selected from a combinatorial chemical library. These substances may be ones whose functions and structures are known or unknown. Whether the candidate substance can be bound with the miR-96-5p is examined by a known method confirming the affinity of the candidate substance with miR-96-5p in vivo, or the candidate substance may be selected by high-throughput screening.

In the case of in vitro screening, the cell of step (b) may be one isolated from an organ expressing EAAC1, which includes brain, spinal cord, kidney, heart or skeletal muscle etc., or a cell line derived from such isolated cell. Especially, HEK293 cell line derived from human kidney is preferable since it express only EAAC1 among EAAT family, and it has to the extent that almost negligible cystine uptake. Although the EAAC1 expressing human cells are likely to also express miR-96-5p, it is preferable to transfect the miR-96-5p oligonucleotide (SEQ ID NO: 1) or miR-96-5p expressing vector into a human cell. On the other hand, in vivo screening targets a brain cell in which miR-96-5p has a negative effect on the GSH content through the expression suppression of EAAC1. In this case, a candidate substance is administered to non-human animal by the methods described for the pharmaceutical composition above.

The measuring of GSH and/or ESSAC1 expression level in step (c) may be performed by detecting and quantifying the expression amount of GSH mRNA or EAAC1 mRNA, which methods include in situ hybridization, Northern blotting, dot blot, RNase protection assay, RT-PCR, Real-Time PCR, qRT-PCT and DNA array analysis. Alternatively, GSH protein and EAAC1 protein are quantified by in situ hybridization, Western blotting, various immune histological methods etc.

The measurement of GSH and/or EAAC1 obtained in step (c) reflects the miR-96-5p inhibitory activity of the candidate substance. The candidate substance of which inhibitory activity is increased compared to the control conditions is determined as miR-96-5p inhibitors. Alternatively, miR-96-5p inhibitory activity of a candidate substance can also be compared to the activity of miR-96-5p inhibitor (oligonucleotide). of the present invention. In this case, a candidate substance having a more than 80% active as the miR-96-5p inhibitor (oligonucleotide) tested under the same screening conditions would be determine as the substance of interest.

Experimental results will be described, which are the basis of the present invention.

EXAMPLES

1. Method
1-1: Animals

Adult male ddY mice (8-10 weeks old) were maintained in a light/dark (LD) 12 h/12 h cycle. The time of 'lights on' is defined as the zeitgeber time (ZT) 0 and the time of 'lights off' is defined as ZT12. All mice were starved 1 day and then perfused intracardially with phosphate-buffered saline (PBS) under $CO_2$ anesthesia. Tissues were collected at ZT 2, 5, 8, 11, 14, 17, 20 and 23. For the dissection of the SCN area, a pyramid of the anterior hypothalamus was dissected out from the ventral surface of the hypothalamus. For the dissection of the SNc area, the brain was cut in half sagittally, and then the area of the mesencephalon was dissected out. All animal protocols were approved by the Animal Experimentation Committee of the Teikyo University School of Medicine.

1-2: Serum Shock

SH-SY5Y and HEK293 cells were grown in Dulbecco's modified Eagle's medium (DMEM) or minimum essential medium (Life Technologies, Frederick, Md.), respectively, supplemented with 10% fetal bovine serum (FBS) and 1% penicillin-streptomycin at 37° C. under 5% $CO_2$. Cells were starved 1 day before serum shock and then changed to a medium containing 50% horse serum and incubated for 2 h, after which the serum-rich medium was replaced with medium containing 10% serum. The time just after the serum shock is defined as time=0.

1-3: Detection of GSH Levels

Brain tissue was homogenized in a 10-fold volume of GSH extraction buffer (5% trichloroacetic acid and 5 mM EDTA) and centrifuged at 1,200×g for 15 min at 4° C. Supernatants were used for measurements. Tissue GSH was detected with 4-fluoro-7-sulfamoylbenzofurazan (Dojindo, Kumamoto, Japan), a fluorogenic labeling reagent for thiols, as described (Non Patent Literatures 45 and 46). The LC-20AD liquid chromatography system (Shimadzu, Kyoto, Japan) was used for GSH detection. An analytical column, Inertsil ODS-2 (150×4.6 mm ID 5 μm) (GL Sciences, Torrance, Calif.), was fixed at 40° C. and connected through a corresponding guard column (10×4.0 mm ID 5 μm; GL Sciences). A stepwise gradient elution was programmed with solvents A (50 mM potassium biphthalate at pH 4.0) and B (8% acetonitrile in solvent A). The mobile phase was held at 80% solvent A and 20% B for 6 min, followed by a 10-min program held at 100% solvent B. The flow rate of the eluate was 1.0 mL/min. All samples were injected into the column with an Auto Injector (Shimadzu). An RF-530 fluorescence spectrometer (Shimadzu) was used with excitation and emission at 380 nm and 510 nm, respectively. The signals from the detector were recorded on a Chromatopac C-R4A (Shimadzu). Tissue GSH concentrations were calculated from the peak area standardized with known amounts of GSH.

For the measurement of GSSG concentration, DTNB-GSSG reductase recycling assay was performed using glutathione quantification kit (Dojindo) according to the manufacture's protocol. The ratio of GSSG to GSH was calculated as dividing GSSG concentration by GSH concentration.

The GSH concentrations in the SH-SY5Y and HEK293 cells were determined by using ThioGlo-1 (Merck, Darmstadt, Germany), a maleimide reagent that produces a highly fluorescent adduct upon reaction with thiol groups. The GSH content was estimated from the fluorescence response via the interaction of ThioGlo-1 mainly with intracellular GSH. Cells were incubated at 37° C. for 30 min with 10 μM ThioGlo-1, and the level of fluorescence was measured using a Multimode Detector DTX800 (Beckman Coulter, Indianapolis, Ind.). To remove the effect of the cystine transport system, 100 μM DTT was added at 1 day before harvesting.

1-4: Viable Cell Count

After the treatment of SH-SY5Y cells with 500 μM $H_2O_2$ or HEK293 cells with 5 mM $H_2O_2$ for 2 h, the cells were suspended the cells with 0.5 mL PBS and placed in a 1.5 mL tube. Next, 0.1 mL of 0.4% Trypan Blue was added and the cells were incubated for 5 min. A hemocytometer was filled with cell suspensions, and at least 100 cells were counted under a microscope. Blue color-stained and non-stained cells were considered damaged and viable cells, respectively.

1-5: Quantitative RT-PCR

RNA isolation was carried out using Trizol Reagent (Life Technologies). For the mRNA quantitation, the inventors conducted reverse transcription (RT) on all individual RNA samples using High-Capacity cDNA Reverse Transcription Kits (Life Technologies) with random hexamers as the RT primers, according to the manufacturer's protocol. Real-time polymerase chain reactions (PCRs) were performed using the Light Cycler 330 (Roche, Mannheim, Germany), and the amplifications were done using the SYBR Premix Ex Taq II (Takara, Shiga, Japan). Primers for quantitative RT-PCR were designed using the Primer3Plus and purchased from Nihon Gene Research Laboratories Inc. (Miyagi, Japan).

For the miRNA quantitation, the miRCURY LNA™ Universal RT microRNA PCR kit (Exiqon, Vedbaek, Denmark) was used for RT-PCR reactions. Real-time PCR for miRNA was performed using PCR primer sets (Exiqon) and SYBR Green master mix (Exiqon) on the LightCycler 480 II (Roche) according to the manufacturer's protocol.

1-6: MiRNA Microarray

A pool of five RNA samples extracted from the mouse mesencephalon at each time point (ZT2, 8, 14 and 20) was analyzed with the SurePrint G3 Mouse miRNA microarray, protocol version 2.2 (Agilent, Santa Clara, Calif.) by Hokkaido System Science Co. (Sapporo, Japan). The platform is based on Sanger miRBase version 16.0, and the number of miRNAs on the chip is 1055.

Scanned microarray raw data were imported into Gene-Spring Gx (Agilent) and then normalized to the 75th percentile per chip. Data in which the signal value was three times more than the error value were chosen for the data analysis. The fold changes of ZT2 vs. ZT8, ZT2 vs. ZT14, ZT2 vs. ZT20, ZT8 vs. ZT14, ZT8 vs. ZT20, and ZT14 vs. ZT20 were used for listing the miRNA candidates.

For the prediction of candidate miRNA that target the 3'-UTR of human, mouse and rat EAAC1, eight established programs which are Diana-microT, miRanda, miRDB, miR-Walk, RNAhybrid, PICTAR, PITA and TargetScan were used.

1-7: Western Blotting

The amount of protein was determined using the BCA protein assay (Thermo Scientific, Rockford, Ill.), and the same amounts of proteins were normalized for total protein. The protein samples were boiled in RIPA buffer (20 mM Tris-HCl pH 7.5, 150 mM NaCl, 1% NP-40, 1% sodium deoxycholate, 0.1% sodium dodecyl sulfate [SDS] and protease inhibitor cocktail; Sigma-Aldrich, St. Louis, Mo.), separated by SDS-polyacrylamide gel electrophoresis (PAGE), and transferred to polyvinylidene fluoride (PVDF) membranes (Bio-Rad, Hercules, Calif.). Nonspecific binding was blocked with 5% skim milk in PBS-Tween20, and proteins were probed with anti-EAAC1 (Abcam, Cambridge, Mass.) at 1:1,000 dilution, anti-PER1 (Abcam) at 1:200, anti-PER2 (Abcam) at 1:1,000, anti-BMAL1 (Abcam) at 1:1,000, anti-CLOCK (Abcam) at 1:1,000 and anti-b-Actin (Sigma-Aldrich) at 1:10,000 dilution. After a wash with PBS-Tween20, the horseradish peroxidase-labeled secondary antibodies were probed and detected with the ECL prime HRP detection kit (GE Healthcare, Piscataway, N.J.). The inventors performed the quantification of the EAAC1 level using a serial dilution of ZT14 samples as the standard curve.

1-8: Luciferase Reporter Assays of miRNA Targeting

The 3'-UTR of human EAAC1 (NM_004170) or mouse EAAC1 (NM_009199) containing five potential target sites for miR-96-5p (SEQ ID NO:1), miR-101a-3p (5'-uacaguacugugauaacugaa-3': SEQ ID NO:2), miR-199a-5p (5'-cccaguguucagacuaccuguuc-3': SEQ ID NO:3) and miR-200a-3p (5'-uaacacugucugguaacgaugu-3': SEQ ID NO:4) were amplified from cDNA of SH-SY5Y cells using forward primer: 5'-GGGAGCTCATAGGCCGGCCCCTGGCT-GCAGATG-3' (seq ID NO:5) and reverse primer: 5'-GCACGCGTCTATGCCGAAAGAATGAGGGAAGT-GTT-3' (SEQ ID NO:6) or mouse mesencephalon using forward primer: 5'-GGGAGCTCATAGGCCATGCCT-GACCTCAGATTGA-3' (SEQ ID NO:7) and reverse primer: 5'-GCACGCGTCTATGCCTAAGGGGA-GAAAGAGTGGG-3' (SEQ ID NO:8), respectively. PCR products amplified with Prime STAR HS (Takara) were cloned into the pMD20 T-vector using Mighty TA-cloning kit (Takara) and then confirmed by DNA sequencing (FAS-MAC, Atsugi, Japan). These inserts were then removed from pMD20-T vector by SacI/MluI digestion (human EAAC1 3'-UTR) or SpeI/MluI digestion (mouse EAAC1 3'-UTR) and then subcloned into the firefly luciferase reporter vector, pMIR-REPORT (Promega, Madison, Wis.). The mutation of the miRNA target sequence on EAAC1 3'-UTR was performed using the Mutagenesis kit (Takara). The primer sequences for mutagenesis were as follows: site1; 5'-TAAT-GTCGGAAAATGTCAATTTTTAAC-3' (Forward) (SEQ ID NO:9) and 5'-GGACAGGGGTCAATTACAGCCTTT-TAC-3' (Reverse) (SEQ ID NO:10), site2; 5'-CAATGTT-GAGTATTGGGACGCTGGTAA-3' (Forward) SEQ ID NO:11) and 5'-CCTAAGAAAAAGTTACAACT-CATAAC-3' (Reverse) (SEQ ID NO:12). Cells were transfected with the appropriate combination of pMIR-human EAAC1 3'-UTR or pMIR-mouse EAAC1 3'-UTR constructs with Renilla luciferase vector (pRL), miRNA mimic and miRNA inhibitor using Lipofectamine RNAiMax (Life Technologies). Firefly luciferase activity was normalized to Renilla luciferase activity. Luciferase activity was measured by a Dual-luciferase Reporter Assay System (Promega) using a luminometer (Turner Biosystems/Promega).

1-9: Immunocytochemistry

The inventors used the chloromethyl reagent 7-amino-4-chloromethylcourmarine (CMAC) (Life Technologies), which produces a highly fluorescent adduct upon reaction with thiol groups for the evaluation of intracellular GSH in SH-SY5Y cells. Cells were incubated at 37° C. for 15 min with 5 µM CMAC and then incubated with serum-free media for 30 min. The cells were then fixed with 4% PFA and then permeabilized with 0.05% Triton-X100 in the case of multiple staining with EAAC1. Non-specific staining was blocked with the reagent PBS containing 1% BSA/0.2% TritonX-100, and the cells were then incubated with anti-EAAC1 (Abcam) at 1:1,000 dilution overnight at 4° C. After a wash with PBS-Tween20, the cells were labeled with fluorescent-labeled secondary antibodies. Finally, the cells were mounted using a Fluoromount-Plus (Diagnostic Biosystems, Pleasanton, Calif.) and captured with a Nikon A1 confocal microscope.

1-10: Intracerebroventricular Injections

The miR-96-5p inhibitor or negative control inhibitor (Exiqon) dissolved in artificial cerebrospinal fluid (aCSF) containing 130 mM NaCl, 3.5 mM KCl, 1.25 mM $NaH_2PO_4$, 2 mM $MgSO_4$, 2 mM $CaCl_2$, 20 mM $NaHCO_3$ and 10 mM glucose (pH 7.4) was administered into the right lateral ventricle of mice. The intraventricular injections were made under stereotaxic guidance. As described (Non Patent Literature 42), a hole was made 0.3 mm caudal to the bregma, 1.2 mm from the midline, and the syringe needle tip was lowered 2.5 mm below the dura. Next, 100 μL of 3.0 nmol of miR-96-5p inhibitor or negative control inhibitor in aCSF was injected intracerebroventricularly for 1 week.

For the experiment on oxidative stress, the brain was immediately cut into 300-mm-thick slices in gassed (95% oxygen/5% $CO_2$) ice-cold aCSF after decapitation. The experiments were initiated by transferring mesencephalic slices to tubes each containing aCSF at 30° C. that was continuously bubbled with 95% oxygen/5% $CO_2$. Mesencephalic slices were exposed to 1 mM 3-morpholinosydnonimine (SIN-1, Santa Cruz Biotechnology, Santa Cruz, Calif.), an NO donor, for 30 min as described (Non Patent Literature 27). The expression of nitrotyrosine was quantified with an OxiSelect™ nitrotyrosine ELISA kit (Cell Biolabs, San Diego, Calif.) according to the manufacturer's instructions.

1-11: Immunohistochemistry

Mice were perfused with PBS containing 4% performaldehyde. Their brains were then placed in optimal cutting temperature (OCT) compound and frozen with liquid nitrogen. Sagittal brain sections were cut on a cryostat at 10 μm thickness and stored at −80° C. The slices were placed in blocking reagent (PBS containing 1% BSA/0.2% TritonX-100) and then incubated overnight at 4° C. with anti-EAAC1 (Alpha Diagnostics, San Antonio, Tex.) at 1:200 dilution and anti-tyrosine hydroxylase (Millipore) at 1:1000 dilution. After a wash with PBS-Tween20, the slices were labeled with fluorescent-labeled secondary antibodies. For nuclear labeling, 4',6-diamidino-2-phenylindole (DAPI) (Dojindo) was used. The section was mounted using a Fluoromount-Plus (Diagnostic Biosystems) and captured with a Nikon A1 confocal microscope.

1-12: Statistics

Data were analyzed by one-way analysis of variance (ANOVA). The diurnal rhythm assessment was further confirmed using the free Cosinor Periodogram analysis program ver.2.3 from Circadian Rhythm Laboratory provided by Dr. R. Reffinetti to determine the circadian periodicity. For the analysis of miRNA mimic or miRNA inhibitor effects, the appropriate statistical test noted in the figure legends was used. Differences with $P<0.05$ were considered significant.

2. Results 2-1: Diurnal Variation of GSH Levels and its Neuroprotective Activity Although a diurnal oscillation of GSH levels in mammalian peripheral organs has been reported (Non Patent Literatures 18-20), little has been reported on GSH rhythm in the central nervous system (Non Patent Literatures 21, 22). In the present study, to measure whether the GSH concentration exhibits a diurnal variation in the mesencephalon, which includes the SNc, the inventors collected tissues every 3 h around the clock. Mice were fasted for 1 day before brain sampling to remove the effects of food consumption. The inventors then observed rhythmic diurnal expression in the mesencephalon. The profile of GSH concentration displayed a diurnal rhythm with 1.2-fold changes (Cosinor; P=0.00018). The highest and lowest GSH levels were observed at midnight (ZT20) and at midday (ZT5), respectively (FIG. 1a).

The diurnal oscillation of the GSH concentration was also exhibited in the SCN (Cosinor; P=0.037), where the central oscillator is located, with the highest values detected at ZT17 and the lowest at ZT11. The diurnal rhythm of GSH levels in the brain exhibited a peak level during the nighttime. A higher GSH level in the nighttime and/or a lower level in the daytime may have important physiological implications.

It has also been reported that the level of GSSG displays a diurnal rhythm in the brain tissue (Non Patent Literature 23), and thus in the present study the inventors also measured the GSSG concentration. As a result, as shown in FIG. 1b, rhythmic changes of the GSSG concentration in the mesencephalon was found (Cosinor; P=0.0021). The phase of its oscillation was similar to the GSH rhythm, with a peak level at ZT17 and a trough at ZT5 (FIG. 1b). The ratio of GSSG/GSH thus exhibits no diurnal rhythm (Cosinor; P=0.57) (FIG. 1c). These results suggest that the determinants of the rhythmic GSH concentration are more closely related to GSH synthesis than to its redox system.

To further investigate the importance of GSH rhythms, the inventors used a serum shock protocol (Non Patent Literatures 24, 25) to synchronize the internal, self-sustained circadian clock of a neuroblastoma cell line, SH-SY5Y, which is commonly used in dopaminergic models. The inventors performed qRT-PCR with the cells collected every 6 h after the serum shock and confirmed that exposure to a high concentration of serum shock induced the expression of a clock gene (Per2) and triggered a rhythmic oscillation (Cosinor; P=0.0028), which is comparable with other cell lines as reported (Non Patent Literatures 24, 25). In the serum-shocked SH-SY5Y cells, the GSH levels displayed oscillation with a period of 24-h cycles (Cosinor; P=0.00023) (FIG. 1d). The peak level was observed 12 h after serum shock, and the next one appeared 36 h later, which is anti-phasic to Per2 expression, and similar to that observed in vivo (FIG. 1a,d).

GSH is one of the most important antioxidants for protection against oxidative stress, and it is possible that its rhythmic oscillation makes neuronal protection and/or vulnerability to stress time-dependent. To test the time-dependent neuroprotection of SH-SY5Y cells, the inventors induced oxidative stress with $H_2O_2$ every 6 h after serum shock. The inventors determined the $H_2O_2$ concentration at 500 μM with half of the cells damaged at a time=0. The percentage of viable cells after $H_2O_2$ exposure fluctuated rhythmically over a period of 24 h (Cosinor; P=0.0003), which is in-phase with GSH rhythm (FIG. 1d,e).

The highest percentage was observed 12 h after serum shock; the next peak appeared 24 h later. This coincident phase between the rhythmic GSH level and viable cell percentages was also observed in non-dopaminergic HEK293 cells, suggesting that the rhythmic oscillation of GSH levels, regardless of cell type, regulates the rhythmic protective activity against oxidative stress.

2-2: Diurnal Fluctuation of EAAC1 Protein Expression

To identify the genes that regulate GSH oscillation, the inventors searched possible gene candidates that encode the major regulatory factor of GSH synthesis, using the NCBI Gene Expression Omnibus (http://www.ncbi.nlm.nih.gov/geo/). They found several GSH regulatory genes whose expression seems to display a circadian rhythm. The inventors then examined the mRNA expression pattern of several candidates during a 24-h period in the mouse mesencephalon and serum-shocked SH-SY5Y cells using qRT-PCR. The mRNA expression patterns of all of the candidate genes turned out to be constitutive.

Figure 2:
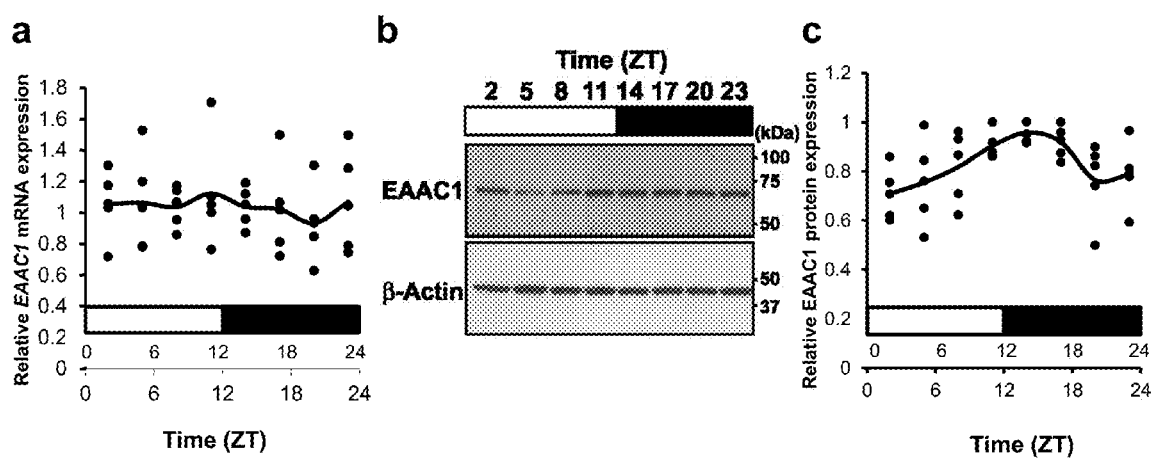
FIG. 2. The expression of EAAC1 in the mouse mesencephalon exhibits a diurnal rhythm at the translational but not transcriptional level. (a) The profile of EAAC1 mRNA expression normalized by Gapdh expression over a 1-day period in mesencephalons examined by qRT-PCR. The bar below the graph indicates the light (white) and dark (black) periods. The data represent mean values and individual data points obtained from five independent experiments. No significant rhythicity was detected (P=0.54). (b) Immunoblots of EAAC1 and β-Actin are shown. Molecular weight markers are depicted to the right. Full-length blots are presented in FIG. 2. (c) Quantification of the data in panel b by densitometry. Data represent mean values and individual data points obtained from five independent experiments and were analyzed by one-way ANOVA and cosinor analysis. A significant diurnal change was detected (P=0.0051).

There are some genes whose protein levels are rhythmic, although their corresponding mRNA is not rhythmic (Non Patent Literature 16). The inventors next examined the protein expression of excitatory amino acid carrier-1 (EAAC1), which is known as a transporter for a rate-limiting precursor of GSH synthesis (Non Patent Literature 5). Interestingly, the protein expression of EAAC1 exhibited a diurnal variation with a peak at ZT14 and a trough at ZT2 in the mesencephalon, although its mRNA expression was arrhythmic (FIG. 2a-c). The amplitude of EAAC1 expression was significantly high, with 1.4-fold changes. This suggests that the expression of EAAC1 is regulated by a post-transcriptional regulation mechanism.

2-3: Diurnal Oscillation of miRNAs that Target the EAAC1 3'-UTR

It was shown that post-transcriptional control could be exerted by miRNAs, which are reported to be crucial modulators of gene expression (Non Patent Literature 14). To identify the miRNAs that regulate the diurnal rhythm of EAAC1 expression, the inventors first screened miRNAs with a diurnal expression pattern using a miRNA microarray. They identified 20 miRNAs with diurnal oscillations (more than 1.5-fold changes) (FIG. 3a) and 106 miRNAs with lower amplitude (1.2-1.5-fold changes).

Among the candidates with diurnal oscillations, the computational analysis of candidate miRNA prediction using established programs revealed three miRNAs-miR-96-5p, miR-199a-5p and miR-200a-3p—as possible candidates, with oscillations that target the 3'-UTR of human, mouse and rat EAAC1. The sequences of these miRNAs' target sites are highly conserved among these animals. The inventors also identified miR-101a-3p as a conserved EAAC1-targeting miRNA candidate, although this miRNA is classified among the lower-amplitude candidates.

Figure 3:
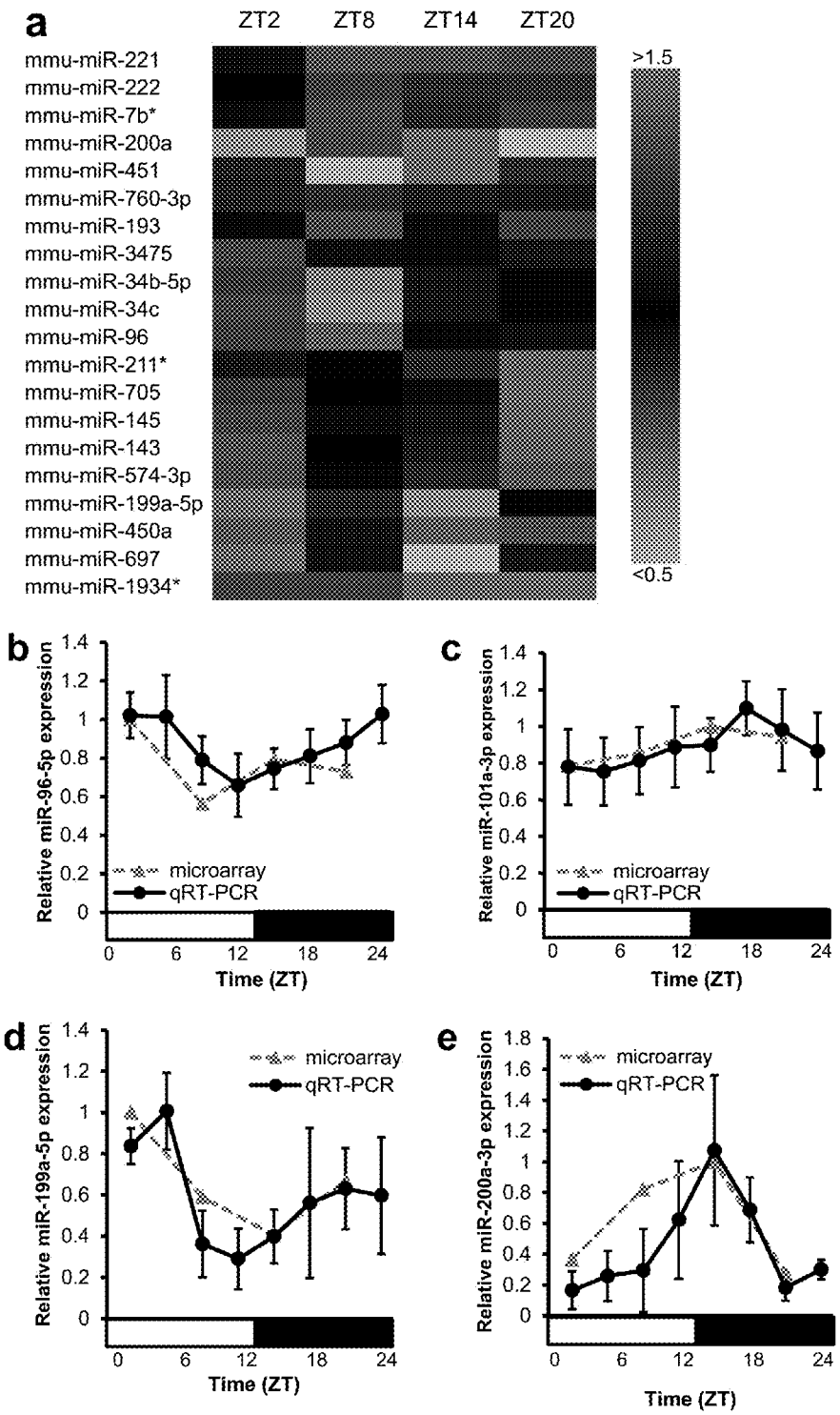
FIG. 3. ist of EAAC1-targeting miRNAs that exhibit diurnal rhythm. (a) The inventors analyzed the pattern of miRNA expression over 24 h in the mesencephalon using a miRNA microarray. A heat map of EAAC1-targeting miRNAs with diurnal expression pattern is shown. The heat scale at the right of the panel represents a linear scale, with magenta, black and turquoise representing high, average and low expression, respectively; Expression profiles of miR-96-5p (b), miR-101a-3p (c), miR-199a-5p (d) and miR-200a-3p (e) over 24 h in mesencephalon examined by a microarray or qRT-PCR. Data represent mean values±s.e.m. obtained from eight independent experiments and were analyzed by a one-way ANOVA and cosinor analysis. Significant rhythmicity of the expression patterns of miR-96-5p and miR-199a-5p miR-200a-3p was revealed (P=0.0082, 0.026 and 0.023, respectively) but not of miR-101s-3p (P=0.053).

Using qRT-PCR, the inventors confirmed that miR-96-5p, miR-199a-5p and miR-200a-3p oscillate in a diurnal manner as shown by the microarray data (Cosinor; P=0.0082, 0.026 and 0.023, respectively) but that miR-101a-3p does not (Cosinor; P=0.053). The miR-96-5p levels reached a maximum at ZT23 and minimum at ZT11, with 1.6-fold amplitude (FIG. 3b). MiR-199a-5p and miR-200a-3p had especially large amplitudes, with more than threefold changes and peaks at ZT5 and ZT14, respectively (FIG. 3d,e). The statistical analysis for rhythmicity revealed that miR-101a-3p had no significant rhythm, although the ANOVA revealed significant variation (ANOVA; P=0.032, Cosinor; P=0.053), suggesting that miR-101a-3p is needed for temporal regulation during a day (FIG. 3c). These oscillations of miRNAs such as miR-96-5p, miR-199a-5p and miR-200a-3p are unique in mature miRNA processing; other miRNAs such as miR-101a-3p exhibit no significant diurnal changes in expression.

2-4: Effect of miRNAs on EAAC1 and GSH Levels

The inventors next examined whether the identified miRNAs regulate GSH levels and EAAC1 expression, using HEK293 cells. They took advantage of the fact that among the EAAT family only EAAC1 is expressed, and that cystine uptake is almost negligible in this cell line (Non Patent Literature 26). They first investigated the effect of miRNA transfection on EAAC1 expression. The transfection of miR-96-5p or miR-101a-3p into HEK293 cells decreased EAAC1 protein compared to control miRNA (Steel's test; P<0.05), whereas miR-199a-5p and miR-200a-3p had no effects on protein expression (FIG. 4a,b).

The inventors then tested miR-96-5p and miR-101a-3p as EAAC1-targeting miRNAs, using a luciferase reporter assay. They made constructs of human or mouse EAAC1 3'-UTR cloned into a luciferase reporter plasmid (FIG. 4c). Consistent with the decreased endogenous expression of EAAC1 by these miRNAs, the luciferase activity was significantly lower when miR-96-5p or miR-101a-3p was transfected (Williams' test; P<0.025) (FIG. 4d). This reduction was blocked by the miRNA inhibitors. Mutation of the core sequence on the EAAC1 3'-UTR target site also blocked the reduction of luciferase activity by miRNAs (FIG. 4e). In contrast, miR-199a-5p and miR-200a-3p had no effect on the luciferase activity, which is also consistent with the western blotting results (FIG. 4a,d).

Finally, The inventors examined whether miR-96-5p and miR-101a-3p affect the GSH level. They transfected miR-96-5p or miR-101a-3p into HEK293 cells and then measured the relative GSH levels. The result showed that the GSH level was significantly decreased by miR-96-5p (Steel's test; P<0.05) but not by miR-101a-3p, suggesting that miR-96-5p regulates GSH levels through EAAC1 3'-UTR (FIG. 4f).

Here are some dissociations between the miRNAs' effect on EAAC1 and that on the GSH level. The miR-96-5p caused a much larger change in EAAC1 than in the actual GSH level. miR-101a-3p had no effect on the GSH level whereas it markedly decreased the EAAC1 level. The inventors' unpublished data revealed that GTRAP3-18 (also known as Addicsin), an inhibitory protein of EAAC1, is reduced by the transfection of miR-101a-3p, suggesting that the bilateral negative effects for EAAC1 and GTRAP3-18 or other inhibitory factors are counteracted so that the change in the GSH level is less than expected.

2-5: Increased GSH and EAAC1 Levels by miR-96-5p Inhibitor

The inventors next investigated the role of endogenous miR-96-5p in SH-SY5Y cells. They transfected miR-96-5p inhibitor and measured the GSH level using same method as in FIG. 4f. No significant change was detected, however, probably because of the low transfection efficiency. To evaluate the intracellular GSH level, they used 7-amino-4-chloromethylcoumarine (CMAC), which fluoresces upon conjugation with GSH after the transfection of the fluorescein-labeled miR-96-5p inhibitor or the negative control inhibitor. As shown in FIG. 5a,b, a significantly higher intensity of CMAC was observed in the cells transfected with miR-96-5p inhibitor compared to the negative control or non-transfected cells (Student's t-test; P<0.05). The expression of EAAC1 was also increased in the cells transfected with miR-96-5p inhibitor (Student's t-test; P<0.05) (FIG. 5c), suggesting that the miR-96-5p inhibitor increased the expression of EAAC1 and GSH level by blocking endogenous miR-96-5p in SH-SY5Y cells. Similar results were obtained using HEK293 cells, namely, the transfection of miR-96-5p inhibitor in HEK293 cells increased the cell viability, GSH level and EAAC1 level 18 or 24 h after the serum shock when the GSH level and protective activity against oxidative stress were lowest. These results suggest that the miR-96-5p inhibitor has a protective role for oxidative stress by increasing EAAC1 and GSH levels in cultured cells.

2-6: Prevention of Neurotoxicity by i.c.v. miR-96-5p Inhibitor

To determine whether miR-96-5p regulates the GSH level via EAAC1 in vivo, the inventors administered an intracerebroventricular injection of miR-96-5p inhibitor to block endogenous miR-96-5p miRNA function. They confirmed that the administered miR-96-5p inhibitor reached the TH-positive dopaminergic neurons in the SNc of the mesencephalon (FIG. 6a). Treatment with miR-96-5p inhibitor for 1 wk significantly increased the expression of EAAC1 (Student's t-test; P<0.05) (FIG. 6b). In addition, the amount of GSH in the mesencephalon at ZT5, when the lowest GSH levels were observed, was also increased compared to the negative control inhibitor injection (Student's t-test; P<0.05) (FIG. 6c). This increased amount of GSH was almost equal to the level at ZT17, when highest the GSH concentration was observed (FIGS. 1a, 6c), indicating that the miR-96-5p inhibitor increased the GSH levels by increasing the EAAC1 expression.

There is another possibility; that is, that the miR-96-5p inhibitor affects core clock components, and that is why the GSH level seems to be increased with the miR-96-5p inhibitor injection as a result of a phase shift even under the LD cycle. The inventors performed western blotting and detected PER1, PER2, BMAL1 and CLOCK. No significant change was observed at ZT5 or ZT17.

Next, the inventors determined whether the miR-96-5p inhibitor has a protective role against oxidative stress in vivo. After the intracerebroventricular injection of either the miR-96-5p inhibitor or a negative control inhibitor, they took mesencephalic slices containing SNc and treated them with SIN-1, generating nitric oxide, which reacts with superoxide to produce peroxynitrite, a potent toxic oxidating/nitrating agent. Nitrotyrosine is a permanent marker of peroxynitrite attack on proteins, revealing oxidative/nitrosative stress damage; treatment with SIN-1 thus increases nitrotyrosine expression (Non Patent Literature 27). As shown in FIG. 6d, the nitrotyrosine levels in the mesencephalon with the injection of the miR-96-5p inhibitor were significantly lower compared to the negative controls.

These results suggest that miR-96-5p inhibitor plays a neuroprotective role in the regulation of GSH levels via EAAC1 expression in the SNc.

3. Discussion

In this study the inventors found that miR-96-5p could be a regulator of the GSH level via EAAC1 to control the reactive oxygen species (ROS) level in the SNc. Reactive oxygen species play an important role in a variety of physiological systems, including the regulation of autophagy, immunity, and differentiation (Non Patent Literature 28). They also act as signaling molecules for cell proliferation, neurogenesis, and circadian rhythm (Non Patent Literature 29). These metabolic pathways requiring ROS in rodents proceed mostly during the daytime (Non Patent Literatures 19, 30-32).

Interestingly, it seems that ROS production also tends to be under circadian control with peak levels during the day (Non Patent Literature 33). Because the overproduction or misregulation of ROS leading to oxidative stress states causes several diseases such as NDs, there must be the regulators for the cycles of ROS build up and elimination. One of these regulators is GSH, which acts as an antioxidant against any form of ROS. Several reports have shown that a circadian clock regulates the GSH level and its enzymes in various organisms (Non Patent Literatures 34-37). Here, the inventors demonstrated that GSH levels also exhibit a diurnal rhythm in the brain, mesencephalon and SCN, reaching a peak during the night, and hitting a trough in the morning (FIG. 1a). The GSH rhythm is anti-phasic, with the rhythm of metabolic events requiring ROS (Non Patent Literatures 19, 30-32), suggesting that rhythmic GSH regulates the diurnal rhythm of ROS activity.

Based on the finding that $H_2O_2$ is a form of ROS and physiologically generated (Non Patent Literature 38), it appears that the effect of $H_2O_2$ would be a reflection of the intracellular antioxidant level. The percentage of viable cells after treatment with $H_2O_2$ is time-dependently correlated with the GSH rhythm, suggesting that GSH is a main determinant of the time-dependent protective activity against oxidative stress in dopaminergic cells and also in other types of cells (FIG. 1d,e). The present results demonstrate that the amplitude of the change in the GSH level is approx. 10%-20%, which is surprising because a 30%-40% decrease in the GSH level in the SNc of PD patients has been reported from several postmortem studies (Non Patent Literatures 4, 39, 40). Basically, the system of diurnal rhythm could be considered to contribute to the efficient use of energy in the human body so that the diurnal oscillation of GSH might be necessary for accelerating the physiological events that need ROS, as well as for minimizing the damage by oxidative stress.

For decades, researchers have studied the molecular circadian clock system composed of a transcriptional/translational feedback loop. In 2005, however, a surprising non-transcriptional circadian system was discovered in cyanobacteria (Non Patent Literatures 41, 42). This non-transcriptional system may also drive circadian rhythms in mammals, although its mechanism is still unclear (Non Patent Literature 43). Here the inventors demonstrated that EAAC1 expression displays diurnal patterns at the translational level despite it being expressed constitutively at the transcriptional level, which is seemingly driven by a non-transcriptional circadian system.

Figure 4:
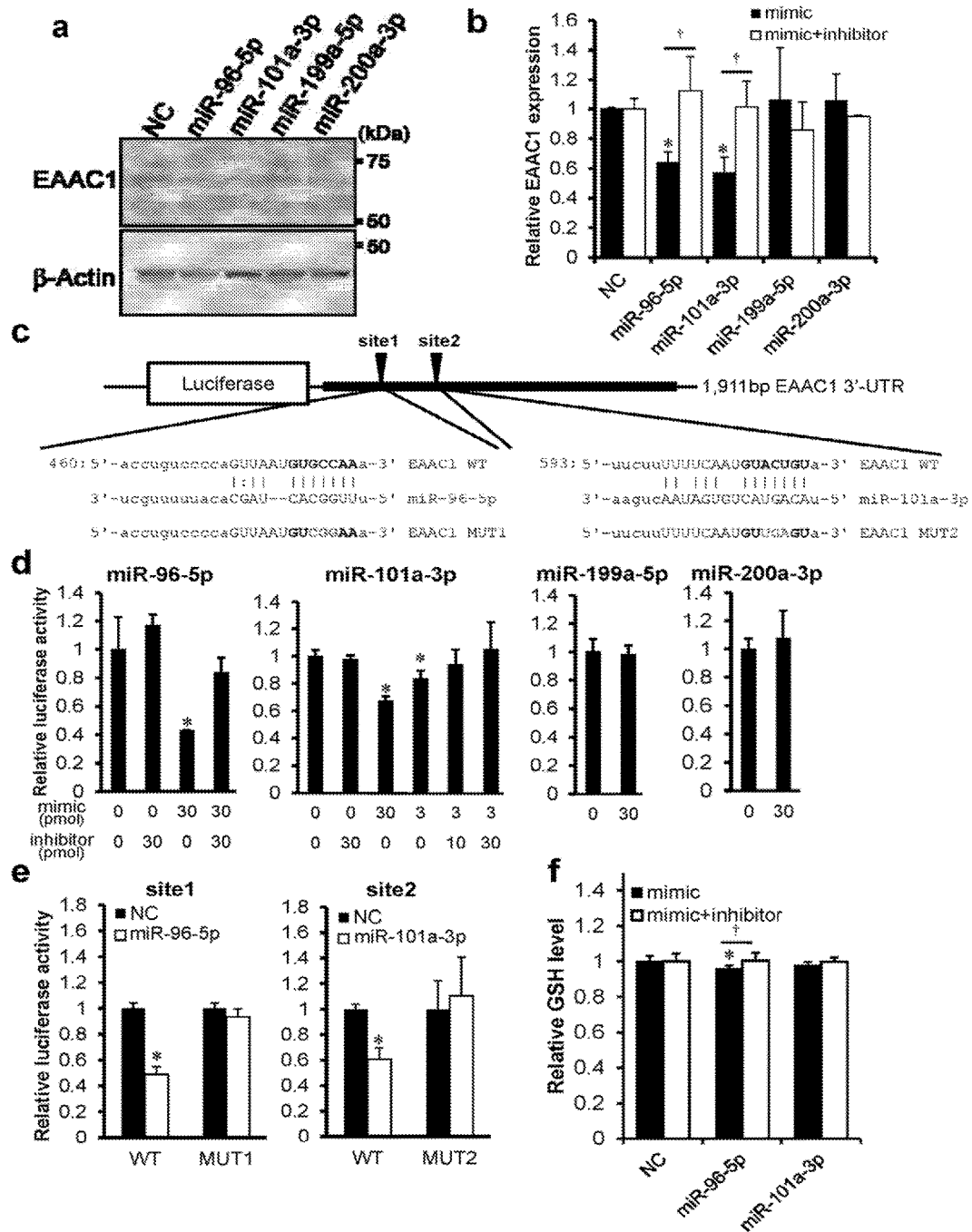
FIG. 4. The effect of miRNA transfection on endogenous EAAC1 expression, GSH level and luciferase reporter gene assay using EAAC1 3'-UTR. (a) The endogenous expressions of EAAC1 and β-Actin in HEK293 cells transfected with each miRNA mimic are shown. NC represents a negative control mimic which has been proven to have no target in human genes. Molecular weight markers are depicted to the right. Full-length blots are presented in Supplementary FIG. 13. (b) Quantification of the data in panel a and Supplementary FIG. 14 by densitometry is shown. Data represent mean values±s.e.m obtained from six independent experiments and were analyzed by Steel's test. *P<0.05 relative to negative control. †P<0.05, effect of miRNA inhibitor. (c) A schematic plot of the luciferase constructs of human EAAC1 3'-UTR. The sequences for the target site of miR-96-5p and miR-101a-3p on EAAC1 3'-UTR region are shown. Mutation was added in a core sequence (bold font) of each miRNA target site on EAAC1 3'-UTR (red font). (d) Relative luciferase activity in SH-SY5Y cells transfected with luciferase constructs in (c) with miRNA mimic (3 pmol or 30 pmol) or inhibitor (10 pmol or 30 pmol) are shown (n=6 for each condition). Data represent mean values±s.e.m. and were analyzed by Williams' test. *P<0.025 relative to negative control. (e) Effects of mutation in target sites of miR-96-5p and miR-101a-3p on luciferase activity (n=6 for each condition). Data are mean values±s.e.m and were analyzed by Student's t-test. *P<0.05 relative to negative control. (f) Effects of miR-96-5p and miR-101a-3p on the GSH level in HEK293 cells (n=10 for each condition). Data are mean values±s.e.m and were analyzed by Steel's test. *P<0.05 relative to negative control. †P<0.05, the effect of the miRNA inhibitor.
Figure 5:
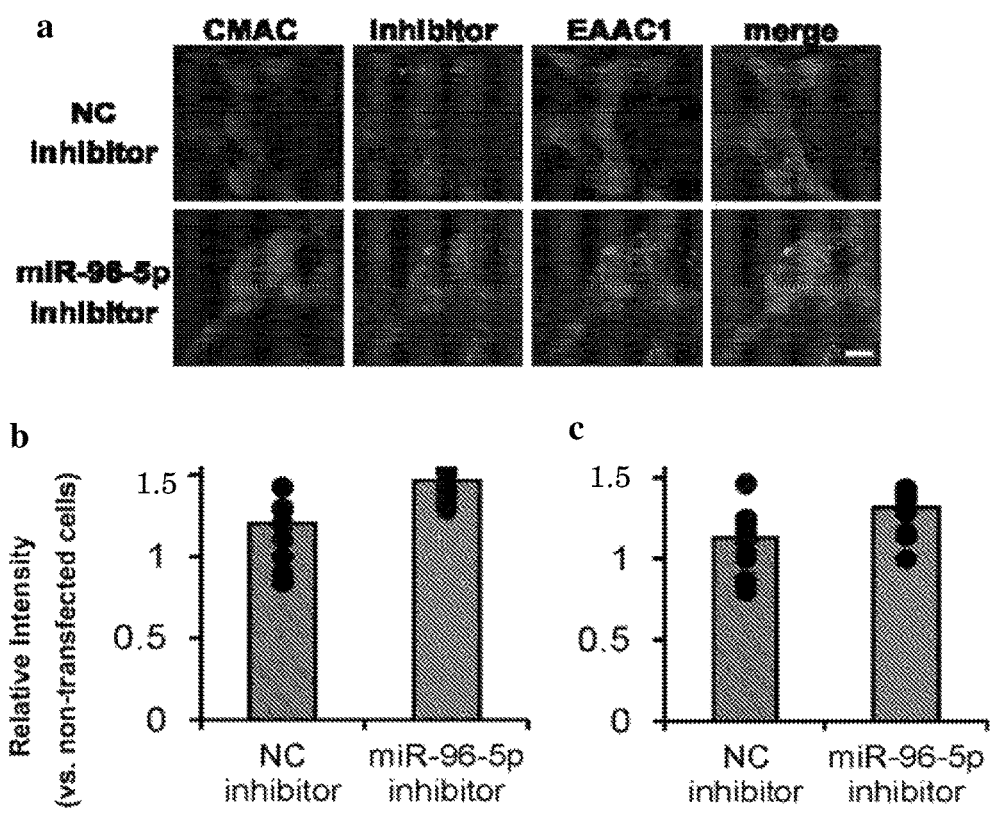
FIG. 5. Effect of miR-96-5p inhibitor transfection on GSH level and EAAC1 expression in SH-SY5Y cells. (a) Confocal images showing the effect of miR-96-5p inhibitor transfection or negative control (NC) inhibitor (green) on the intensity of CMAC as a marker of GSH (blue) and EAAC1 expression (red). The miR-96-5p inhibitor increased the CMAC and EAAC1 levels compared to the NC inhibitor. Scale bar: 10 μm. (b,c) The density of CMAC (b) and EAAC1 level (c) (n=11; 10-20 cells were measured in each sample). Data are mean values and individual data points and were analyzed by Student's t-test. *P<0.05 relative to NC inhibitor. The number of individual data points is the same as the sample size although some points overlap.
Figure 6:
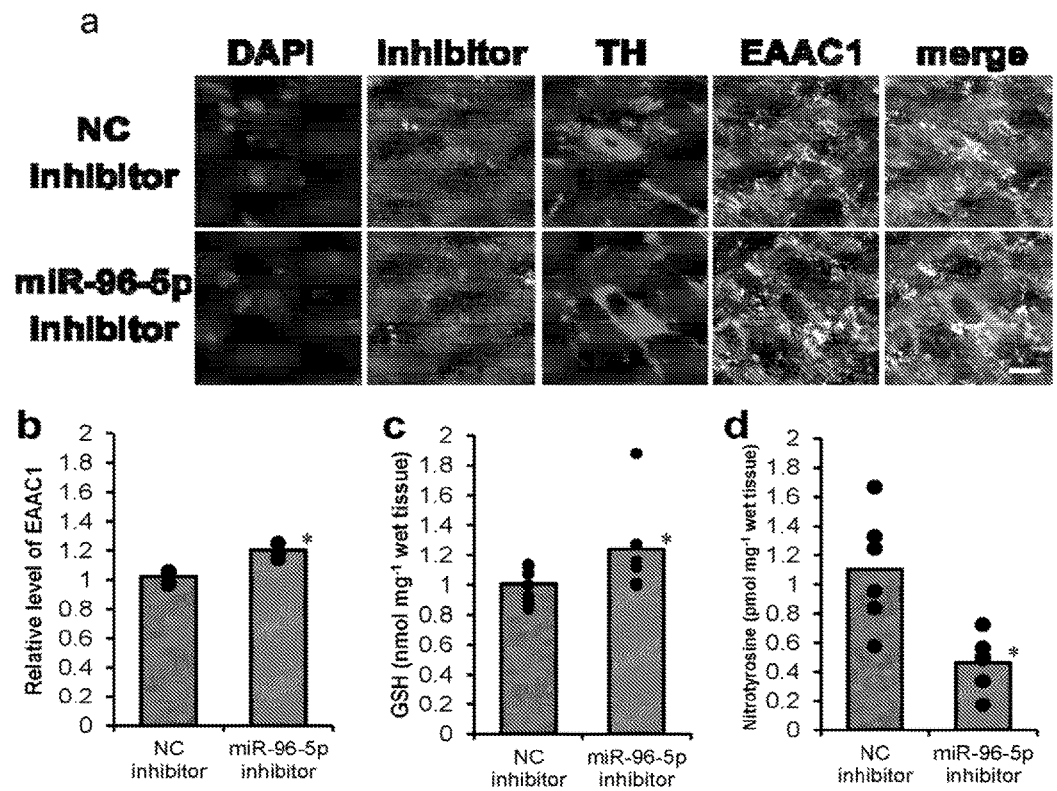
FIG. 6. Effect of the intracerebroventricular administration of miR-96-5p inhibitor on the GSH level, EAAC1 expression and neuroprotection in vivo. (a) Confocal images showing the effect of miR-96-5p inhibitor administration or negative control (NC) inhibitor (green) on EAAC1 expression (yellow). The inhibitors were administered intracerebroventricularly for 1 wk. The brains were then fixed at ZT5 when the lowest GSH amount was observed, and were sagittally sliced. Tyrosine hydroxyrase (red) was used for the dopaminergic neurons marker. The nuclei were stained with DAPI (blue). The miR-96-5p inhibitor increased the amount of EAAC1 compared to the NC inhibitor. Scale bar: 10 μm. (b) The density of EAAC1 expression of TH-positive neurons (n=3; 50-100 neurons per sample). Data are mean values and individual data points and were analyzed by Student's t-test. *P<0.05 relative to NC inhibitor. (c) The GSH levels in mesencephalon after the administration of NC or miR-96-5p inhibitor (NC inhibitor; n=10, miR-96-5p inhibitor; n=6). Data are mean values and individual data points. The data were analyzed by Student's t-test. *P<0.05 relative to the NC inhibitor. (d) The level of nitrotyrosine expression in mesencephalon with the injection of either miR-96-5p inhibitor or NC inhibitor. Data are mean values and individual data points and were analyzed by Student's t-test. *P<0.05 relative to the NC inhibitor. The number of individual data points is the same as the sample size although some points overlap.

The inventors also found that the diurnal expression of EAAC1 is regulated by post-transcriptional regulators, miRNA (FIGS. 4-6). The latest miRbase (Release 20) reported 30,424 mature miRNA products; 24,521 precursor hairpin miRNAs have been found so far, and the number of miRNAs is still increasing. Since the expression profile of miR-96-5p exhibits a diurnal rhythm (FIG. 3b), the inventors searched five kilobases upstream of the miR-96-5p encoding region, but found no important cis-element (E-box and RORE sequences) for circadian regulation. Thus, miRNA-processing genes such as Dicer, Drosha and Ago2 may play an important role in composing the circadian rhythm of miRNA. The inventors infer miRNA to be one of the most important components in the non-transcriptional circadian system.

Finally, the inventors administered intracerebroventricular injections of a miR-96-5p inhibitor and observed an increase in the GSH level along with an increased EAAC1 expression in the TH-positive neurons of the mouse SNc (FIG. 6). Moreover, the injection of the miR-96-5p inhibitor involves a protective effect against oxidative stress by SIN-1.

These results are quite interesting in that the miR-96-5p inhibitor injection could be a therapeutic agent for increasing GSH levels in the brain. It has not been thought possible to increase GSH levels in the brain through the extracellular administration of GSH itself or its precursor cysteine (Non Patent Literature 5). Thus, at present, N-acetyl-L-cysteine is the only effective agent for increasing GSH levels with low toxicity in order to increase the lifespan of an aging mouse model (Non Patent Literatures 9, 44). MiR-96-5p inhibitors could be another option. Further research is needed to confirm this possibility.

The invention claimed is:

1. A method for increasing an expression of glutathione (GSH) in the brain of a subject by administering a miRNA-96-5p inhibitor into the brain of the subject, wherein the miRNA-96-5p inhibitor is an oligonucleotide at least partially complementary to the nucleotide sequence of SEQ ID NO:1.

2. The method of claim 1, wherein the miRNA-96-5p inhibitor is an antisense oligonucleotide for the sequence of SEQ ID NO:1.

3. A method for treating a neurodegenerative disease caused by decrease of glutathione (GSH) amount or depression of GSH activity, which comprises administrating a miRNA-96-5p inhibitor into the brain of a subject, wherein the miRNA-96-5p inhibitor is an oligonucleotide at least partially complementary to the nucleotide sequence of SEQ ID NO:1.

4. The method of claim 3, wherein the miRNA-96-5p inhibitor is an antisense oligonucleotide for the sequence of SEQ ID NO:1.

5. The method of claim 3, the disease is a neurodegenerative disease caused by an oxidative stress in the brain.

* * * * *